US007378259B2

(12) United States Patent
Bahatt et al.

(10) Patent No.: US 7,378,259 B2
(45) Date of Patent: May 27, 2008

(54) FLUID PROCESSING DEVICE

(75) Inventors: Dar Bahatt, Foster City, CA (US); Debjyoti Banerjee, Fremont, CA (US)

(73) Assignee: Applera Corporation, Foster City, CA (US)

( * ) Notice: Subject to any disclaimer, the term of this patent is extended or adjusted under 35 U.S.C. 154(b) by 310 days.

(21) Appl. No.: 10/891,650

(22) Filed: Jul. 15, 2004

(65) Prior Publication Data

US 2006/0013742 A1 Jan. 19, 2006

(51) Int. Cl.

| | |
|---|---|
| *C12P 19/34* | (2006.01) |
| *C12P 19/36* | (2006.01) |
| *C12P 19/30* | (2006.01) |
| *C12Q 1/68* | (2006.01) |
| *G01N 33/00* | (2006.01) |

(52) U.S. Cl. ......................... 435/91.1; 436/43; 436/94; 435/6; 435/89; 435/90

(58) Field of Classification Search ................. 436/94, 436/43; 435/6, 89, 90, 91.1

See application file for complete search history.

(56) References Cited

U.S. PATENT DOCUMENTS

| | | | | |
|---|---|---|---|---|
| 5,429,807 | A | 7/1995 | Matson et al. | |
| 5,436,327 | A | 7/1995 | Southern et al. | |
| 5,681,484 | A | 10/1997 | Zanzucchi et al. | |
| 5,700,637 | A | 12/1997 | Southern | |
| 6,506,558 | B1 | 1/2003 | Fodor et al. | |
| 6,586,211 | B1 | 7/2003 | Stähler et al. | |
| 6,632,399 | B1 | 10/2003 | Kellogg et al. | |
| 6,670,127 | B2 * | 12/2003 | Evans | 435/6 |
| 6,818,395 | B1 * | 11/2004 | Quake et al. | 435/6 |
| 6,911,345 | B2 * | 6/2005 | Quake et al. | 436/532 |
| 6,917,882 | B2 * | 7/2005 | Selifonov et al. | 702/19 |
| 7,024,312 | B1 * | 4/2006 | Selifonov et al. | 702/19 |

OTHER PUBLICATIONS

Mehnaaz F. Ali et al., "DNA Hybridization and Discrimination of Single-Nucleotide Mismatches Using Chip-Based Microbead Arrays," *Analytical Chemistry*, vol. 75, No. 18, pp. 4732-4739, Sep. 15, 2003.

(Continued)

*Primary Examiner*—Brian Sines

(57) ABSTRACT

A fluid processing device and method of using the device are provided. The fluid processing device can include a substrate with a fluid processing pathway at least partially formed in or on the substrate. The fluid processing pathway can include an input end, at least one output end, a first input opening, a plurality of reaction sites each in fluid communication with the first input opening and arranged between the first input opening and the at least one output end. The fluid processing pathway can include a plurality of second input openings including two or more in fluid communication respectively with each of the reaction sites, the second input openings being arranged with the reaction site disposed between the at least one output end and the second input openings. The fluid processing device can include one or more output openings in fluid communication with one or more of the plurality of reaction sites and arranged at the at least one output end of the fluid processing pathway.

29 Claims, 4 Drawing Sheets

OTHER PUBLICATIONS

Pei Yu Chiou et al., "*Optical Actuation of Microfluidics Based on Opto-Electrowetting*," Solid-State Sensor, Actuator and Microsystems Workshop, Hilton Head Island, South Carolina, pp. 269-272, Jun. 2-6, 2002.

Pei Yu Chiou et al., "*Pico Liter Droplet Manipulation Based on a Novel Continuous Opto-Electrowetting Mechanism*," http://photonics.ucla.edu/pdf/IPL_UCLA-PeiyuChiou-Transducers-2003-id5.pdf, (four pages) printed on Jan. 28, 2004.

"*Microfluidics*," Xeotron, http:—www.xeotron.com-fw-main-default.asp?DocID=18, (two pages) printed on Jan. 28, 2004.

In situ *Synthesis-based Microarray Manufacturing*, NimbleGen™ Systems, Inc. http:—www.nimblegen.com-technology-manufacture.html, (three pages) printed on Jan. 28, 2004.

Notification of Transmittal from PCT Application No. PCT/US05/20227.

International Search Report dated Feb. 26, 2007, from PCT Application No. PCT/US05/20227.

Written Opinion of International Searching Authority dated Feb. 26, 2007, from PCT Application No. PCT/US05/20227.

* cited by examiner

FLUID PROCESSING DEVICE

FIELD

The present teachings relate to fluid processing devices and methods of processing fluid samples.

BACKGROUND

For various chemical and biochemical processes and analysis, the synthesis of one or more custom polynucleotide or oligonucleotide, is required. Scalable, directly addressable devices, and methods for the synthesis of a custom polynucleotide, would be desirable.

SUMMARY

According to various embodiments, a fluid processing device is provided that includes a substrate, a fluid processing pathway at least partially formed in or on the substrate, and one or more output openings arranged at the output end of the fluid processing pathway and in fluid communication with one or more of a plurality of reaction sites included in the fluid processing pathway. According to various embodiments, the fluid processing pathway includes an input end, at least one output end, a first input opening, a plurality of reaction sites each in fluid communication with the first input opening and arranged between the first input opening and the at least one output end, and a plurality of second input openings including two or more in fluid communication, respectively, with each of the reaction sites. The second input openings can be arranged such that at least one respective reaction site is disposed between the at least one output end and the second input openings.

According to various embodiments, a fluid processing device is provided that includes a substrate and a fluid processing pathway at least partially formed in or on the substrate. The fluid processing pathway can include a first input opening, a plurality of reaction sites each in fluid communication with the first input opening and each containing a high surface area support material, a plurality of second input openings, at least one output chamber in fluid communication with each of the reaction sites, and at least one output opening formed in the at least one output chamber. According to various embodiments, each of the second input openings is in fluid communication with a respective one of the plurality of reaction sites.

According to various embodiments, a fluid processing device is provided that includes a first input opening, an input chamber in fluid communication with the first input opening including at least a first fluid-contacting surface, at least one reaction chamber in fluid communication with the input chamber and including at least a second fluid-contacting surface, at least one waste chamber in fluid communication with the at least one reaction chamber and including at least a third fluid-contacting surface. The second fluid-contacting surface can exhibit a greater hydrophilicity than the first fluid-contacting surface, and the third fluid-contacting surface can exhibit a greater hydrophilicity than the second fluid-contacting surface.

According to various embodiments, a method of synthesizing a polynucleotide is provided. The method can include providing a fluid processing device comprising a reaction chamber and first and second input openings in fluid communication with the reaction chamber. The method can include introducing a first nucleotide monomer into the second input opening of the fluid processing device, moving the first nucleotide monomer by capillary action from the second input opening into the reaction chamber, attaching the first nucleotide monomer to a support disposed in the reaction chamber to form a first supported nucleotide monomer, introducing a first deprotecting reagent into the first input opening, moving the first deprotecting reagent by capillary action from the first input opening into the reaction chamber to form a deprotected first nucleotide monomer in the reaction chamber, introducing a wash reagent into the first input opening, moving the wash reagent by capillary action from the first input opening into the reaction chamber, moving the first deprotecting reagent out of the reaction chamber, introducing a second nucleotide monomer into the second input opening, moving the second nucleotide monomer by capillary action from the second input opening into the reaction chamber, introducing a wash reagent into the first input opening, moving the wash reagent by capillary action from the first input opening into the reaction chamber, moving the wash reagent out of the reaction chamber, and contacting the second nucleotide monomer with the deprotected first nucleotide monomer in the reaction chamber to form a second supported nucleotide monomer.

According to various embodiments, a method of synthesizing a polynucleotide is provided. The method can include providing a fluid processing device comprising a reaction chamber and first and second input openings in fluid communication with the reaction chamber. According to various embodiments, the method can include introducing a first nucleotide monomer into the second input opening of the fluid processing device, moving the first nucleotide monomer by centripetal force from the second input opening into the reaction chamber, attaching the first nucleotide monomer to a support disposed in the reaction chamber to form a first supported nucleotide monomer, introducing a first deprotecting reagent into the first input opening, moving the first deprotecting reagent by centripetal force from the first input opening into the reaction chamber to form a deprotected first nucleotide monomer in the reaction chamber, moving the first deprotecting reagent out of the reaction chamber, introducing a first wash reagent into the first input opening, moving the first wash reagent by centripetal force from the first input opening into the reaction chamber, introducing a second nucleotide monomer into the second input opening, moving the second nucleotide monomer by centripetal force from the second input opening into the reaction chamber, introducing a second wash reagent into the first input opening, moving the second wash reagent by centripetal force from the first input opening into the reaction chamber, moving the wash reagent out of the reaction chamber, and contacting the second nucleotide monomer with the deprotected first nucleotide monomer in the reaction chamber to form a second supported nucleotide monomer.

BRIEF DESCRIPTION OF THE DRAWINGS

Various embodiments of the present teachings are exemplified by the accompanying drawings. The teachings are not limited to the embodiments depicted, and include equivalent structures and methods as set forth in the following description and as would be known or recognized by those of ordinary skill in the art given the present teachings. In the drawings.

Figure 1:
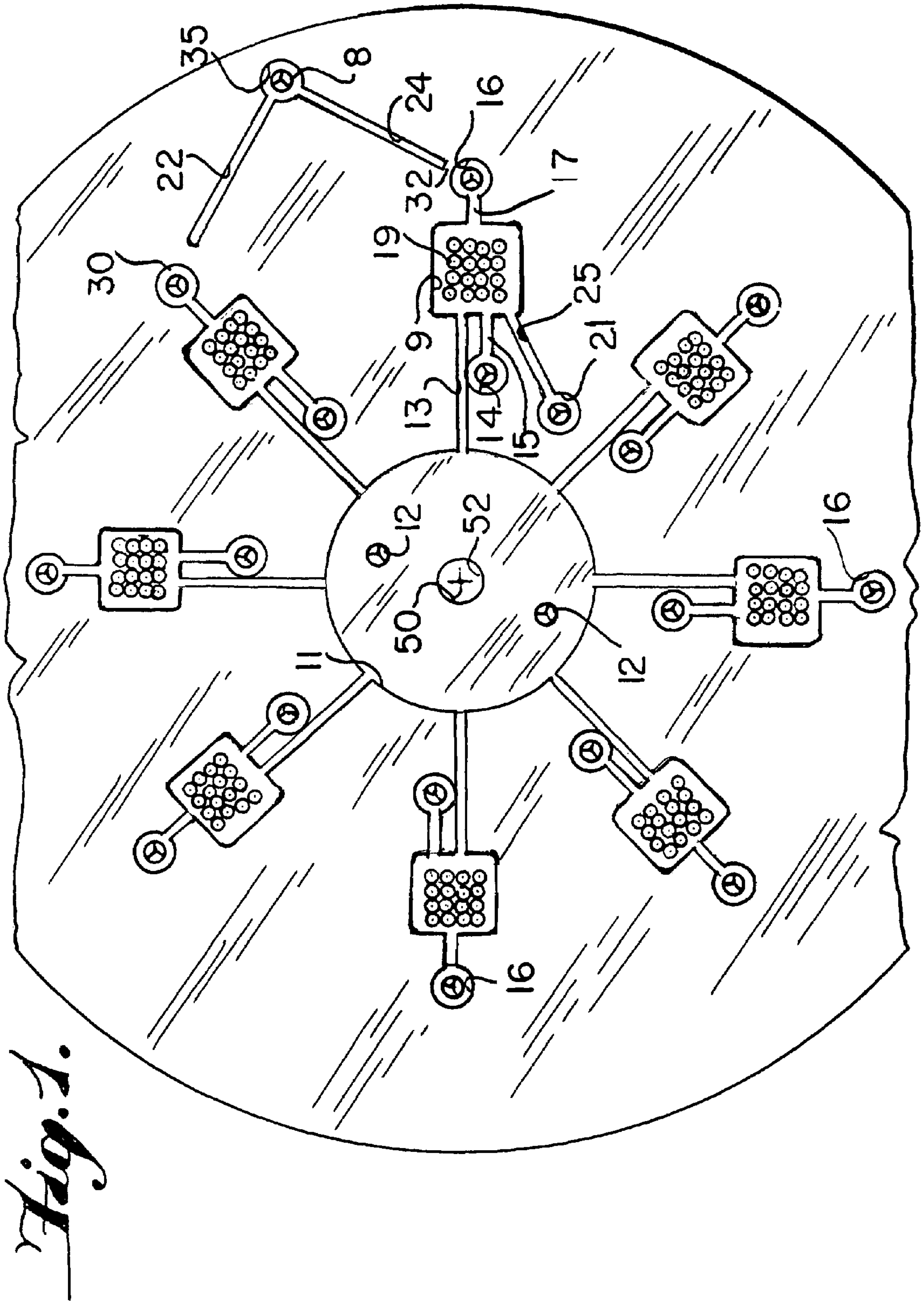
FIG. 1 is a top plan view of a fluid processing device according to various embodiments.

It is to be understood that both the foregoing general description and the following detailed description are exemplary and explanatory only, and are intended to provide an explanation of various embodiments of the present teachings.

DETAILED DESCRIPTION OF EXEMPLARY EMBODIMENT

According to various embodiments, a fluid processing device is provided that is capable of manipulating fluids with capillary action or centripetal force through process steps that result in synthesized oligonucleotide. The device can include a substrate, a fluid processing pathway at least partially formed in or on the substrate, and one or more output openings arranged at the output end of the fluid processing pathway and in fluid communication with one or more of a plurality of reaction sites included in the fluid processing pathway. According to various embodiments and as will be even more apparent from the description of the drawing FIGS. that follows, the fluid processing pathway can include an input end, at least one output end, a first input opening, a plurality of reaction sites each in fluid communication with the first input opening and arranged between the first input opening and the at least one output end, and a plurality of second input openings including two or more in fluid communication respectively with each of the reaction sites. The second input openings can be arranged with the reaction site disposed between the at least one output end and the second input openings.

According to various embodiments, the fluid processing device may further include at least one valve arranged between at least one of the second input openings and at least one of the reaction sites. The fluid processing device can include a plurality of valves, and at least one valve can be provided between each of the second input openings and the reaction sites. The fluid processing device can include a plurality of fluid passageways that provide a fluid communication between one of the plurality of second input openings and a respective one of the reaction sites.

According to various embodiments, the fluid processing device can include a high surface area support material in each of the plurality of reaction sites. Each of the reaction sites can include at least one sidewall, and the high surface area support material can include the at least one sidewall. The high surface area support material can instead, or additionally, include, for example, controlled pore size glass, a porous glass, a gel, a hydrogel, or a combination thereof According to various embodiments, the first input opening and each of the plurality of second input openings of the fluid processing device can be sealed openings. The fluid processing device can include a cover layer that at least partially seals the first input opening and the plurality of second input openings. Appropriate ports, septa, or other openings or recloseable openings can be provided at each of the input openings.

According to various embodiments, the fluid processing device can include one or more valves capable of interrupting fluid communication between one or more first output openings and one or more of the plurality of reaction sites. The output end of the fluid processing device can include a plurality of output ends and the one or more output opening can include a plurality of output openings arranged at the plurality of output ends.

According to various embodiments, the fluid processing device can include an axis of rotation, and with respect to the axis of rotation, the plurality of reaction sites can be arranged radially outward of the first input opening and of the plurality of second input openings, and the one or more output opening can be arranged radially outward of at least one of the reaction sites.

According to various embodiments, the various channels, inlets, outlets, chambers, and reaction sites described herein can have any of a variety of dimensions. At least one feature can have at least one dimension of one mm or less, for example, 500 microns or less. Channel depths and widths can be equivalent or different from one another. Different channel aspect ratios can be used. According to embodiments of devices that are capable of capillary action manipulation of fluids, the devices can include dimensions that promote or induce capillary fluid flow. The channels can have various cross-sectional shapes, including, for example, a square cross-section, a rectangular cross-section, a circular cross-section, a U-shaped cross-section, a V-shaped cross-section, or a combination thereof.

According to various embodiments, for example, the embodiment shown in FIG. 1, a fluid processing device can be provided that includes one or more first input opening 12, and an input chamber 11 in fluid communication with each first input opening 12. A fluid pathway 13 can provide a fluid communication between the input chamber 11 and a reaction site 9. One or more second input openings 14 can be provided in fluid communication with the reaction site 9, for example, through channel 15. The reaction site 9 can be in fluid communication with an output opening 16 via channel 17.

According to various embodiments, the fluid processing device can include a plurality of second input openings in fluid communication with the reaction site 9, for example, to include second input opening 21 in fluid communication with reaction site 9 by way of channel 25.

According to various embodiments, the fluid processing device can include a fluid communication or channel 17 between the reaction site 9 and the output opening 16. As can be seen, two or more output openings 16 or their related chambers can be pooled to output chamber 35, for example, through channels 22, 24 and Zbig valves 30, 32. Zbig valves 30, 32 are described in U.S. patent application Ser. No. 10/336,274, which is incorporated herein in its entirety by reference.

According to various embodiments, as shown in FIG. 1, the fluid processing device can have a central axis of rotation 50 and a centering hole 52. The device can include a plurality of reaction sites 9 arranged radially outward of the input chamber 11. The output openings 16 can be arranged radially outwardly of the reaction sites 9. The second input openings 14 can be arranged radially inwardly with respect to the respective reaction chambers 9. According to various embodiments, the number of reaction sites 9 can be limited only by manufacturing constraints.

According to various embodiments, one or more of the channels or fluid communications can have one or more dimensions sufficiently small to promote capillary action movement of an aqueous sample therethrough.

Figure 2:
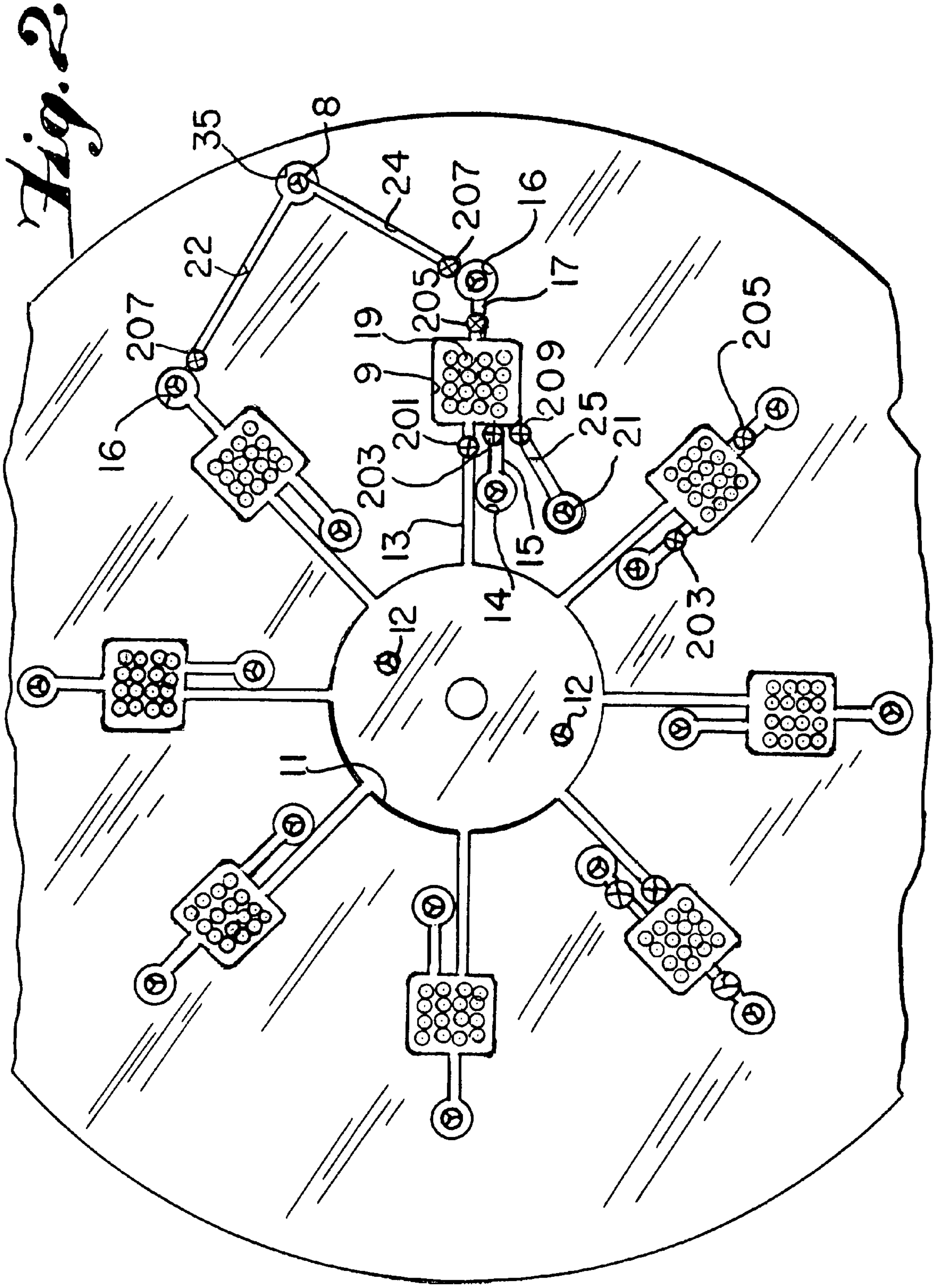
FIG. 2 is a top plan view of a fluid processing device including valving according to various embodiments.

FIG. 2 illustrates an embodiment of the fluid processing device including one or more valves 201, 203, 205, and 207, each capable of interrupting fluid communication along a fluid pathway. Valve 201 controls the flow of fluids from an input opening 12 to a reaction site 9 along a fluid pathway 13. The valve 203 controls the flow of fluids from a second input opening 14 to the reaction site 9 along a fluid pathway 15. The valve 205 controls the flow of fluids from the reaction site 9 to an output opening 16 along a fluid pathway 17. Valves 207 control the flow of fluids from the output chambers 16 to the pooled output chamber 35 along fluid pathways 22, 24. Valve 209 controls the flow of fluids from a second input opening 21 to the reaction site 9 along a fluid pathway 25. According to various embodiments, suitable valving is taught, for example, in U.S. patent applications Ser. Nos. 10/336,274, 10/403,652, 10/625,449, and 10/403, 640, which are incorporated herein in their entireties by reference.

Figure 3:
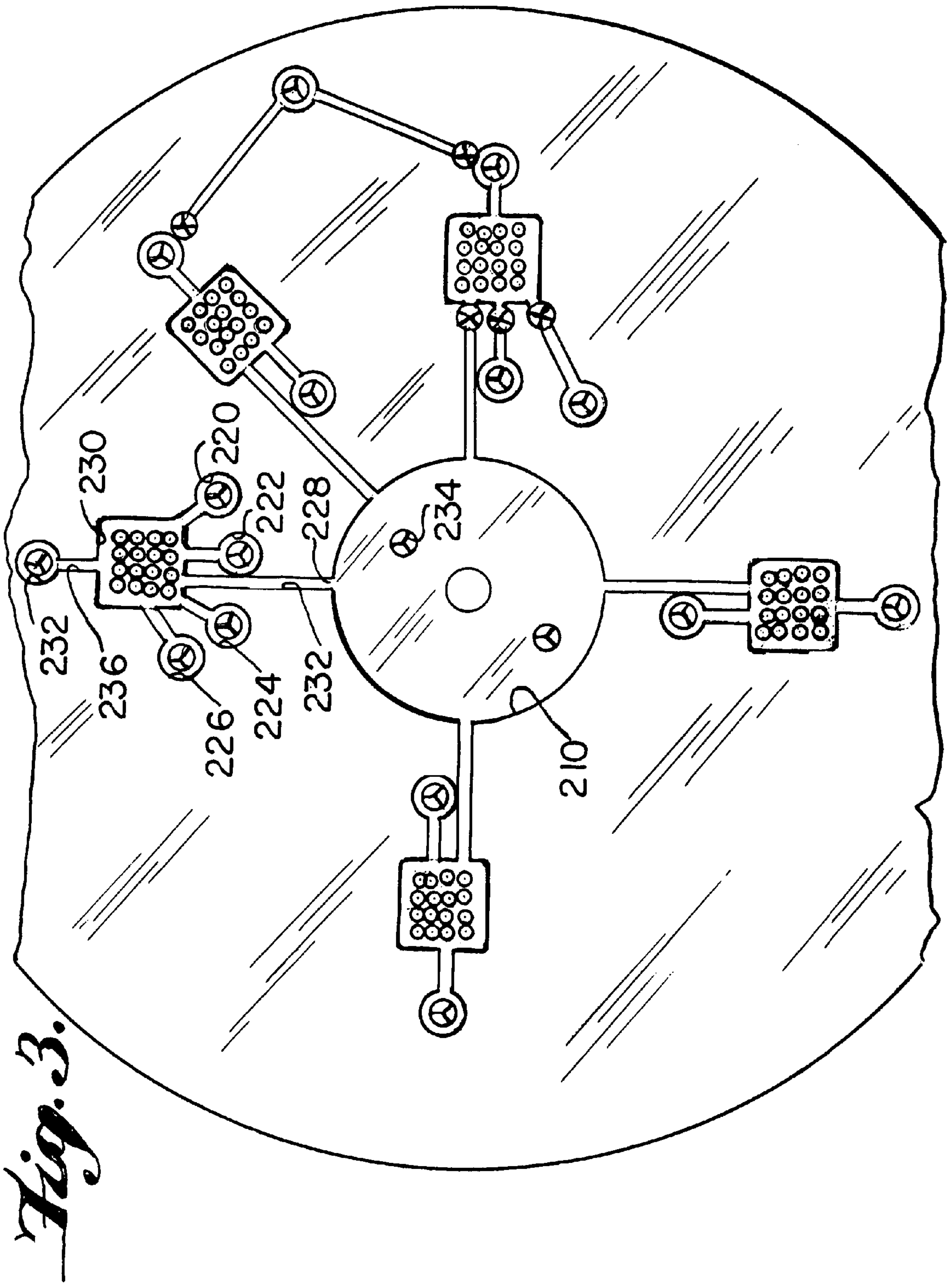
FIG. 3 is a top plan view of a fluid processing device according to various embodiments.

FIG. 3 is a top plan view of an embodiment of a device that includes a plurality of different polynucleotide synthesis pathways. Exemplary devices can include a plurality of any one of the types of synthesis pathways shown in FIG. 3. The device can include a plurality of a single type of synthesis pathways.

According to various embodiments, a synthesis device is provided that includes a first input opening 228, a reaction site 230, an outlet 232, and a plurality of second input openings 220, 222, 224, 226. The device can include a fluid communication 232 between the first input opening 228 and the reaction site 230. The device can include a fluid communication 236 between the reaction site 230 and the outlet 232. The device can also include fluid communications between the second input openings and the reaction site 230. The first input opening 228 can include a common well or common loading chamber 210 that can be provided with one or more entrance openings, such as one or more septa 234. The second input openings 220, 222, 224, 226 can be fluidly connected to nucleotide monomer building block supply lines that can independently load different respective monomers. The outlet 232 can be provided with a septum and can be placed in fluid communication with an outlet or waste removal line or device. The common chamber 210 can surround a central opening in the device that can be used to hold the device on a central axis of rotation, for example, on a rotating platen. Supplies of wash reagent, deep protecting reagent, and the like, can be independently fluidly connected to the common chamber 210. The supply and removal lines can remain fluidly connected to the device during a synthesis procedure, for example, when capillary action is the moving force for manipulating liquids through the device.

According to various embodiments, a device including a synthesis pathway and including the inlets and outlets to reaction site 30 depicted in FIG. 3 is provided, held on a rotatable platen of a processing system. The system can include separate injectors connected to supply lines, and a positioning system for respectively positioning the injectors with respect to second input openings 220, 222, 224, and 226, respectively, and, for example, for positioning an injector with respect to septum 234. The system can also include an output line and positioning system for positioning the output line with respect to outlet 232 or the septum thereof The system can include a drive unit for rotating the rotatable platen, and a holder for holding the device on the rotatable platen during rotation. This system can also include pumps for supplying the various reagents and building blocks to the respective inputs, and for removing waste, product, or both, from the synthesis pathway outlet.

Figure 4:
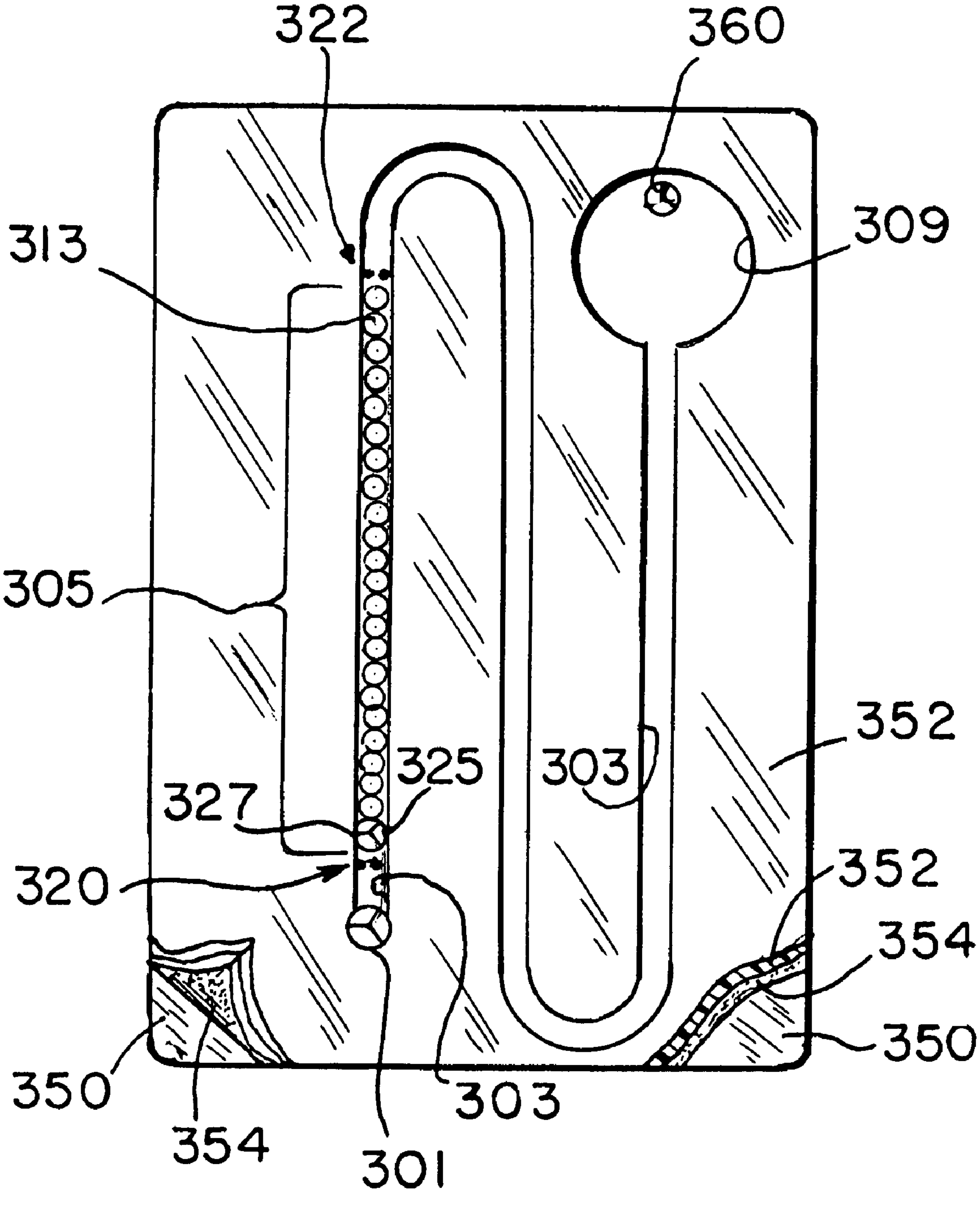
FIG. 4 is a top plan view of a fluid processing device according to various embodiments.

According to various embodiments, for example, according to the embodiment shown in FIG. 4, a fluid processing device can be provided that can include a first input opening 301 including a septum 302, a first channel 303, a reacton chamber 305, a second channel 307, and a waste chamber 309. The device can include a substrate 350, a cover layer 352, and an adhesive layer 354 that bonds the cover layer 352 to the adhesive layer 354. The waste chamber 309 can include a vent 360, for example, to exhaust displaced gas from the waste chamber 309. The vent 360 can include a hydrophobic material.

According to various embodiments, the reaction chamber 305 can include high surface area support material 313, for example, porous beads, that provides a high surface area on which a desired synthesis reaction to occur. According to various embodiments, the support material can be retained in the reaction chamber 305 by weirs 320, 322. The reaction chamber 305 can include an extraction port 325, for example, including a septum 327, for removing the support material following a synthesis reaction. A channel 303 can exhibit an increasing hydrophilicity in a direction from the first input opening 301 toward the waste chamber 309. The channel 303 can include a first fluid-contacting surface, for example, the surface of the portion of the channel that defines the reaction chamber 305. The first fluid-contacting surface can have the same or a lower hydrophilicity than a second fluid-contacting surface of the first channel 303. The second fluid-contacting surface can be, for example, the portion of the channel 303 from the weir 322 to the end of the channel 303 at waste chamber 309. The waste chamber 309 can include a third fluid-contacting surface. The third fluid-contacting surface can have a greater hydrophilicity than the first and the second fluid-contacting surfaces.

According to various embodiments, the volume of the waste chamber 309 can be greater than the volume of the reaction chamber 305, for example, at least about ten times greater than the volume of the reaction chamber 305. According to various embodiments, the high surface area support material 313 present in the reaction chamber 305 can include, for example, controlled-pore size glass, porous glass, a gel, a hydrogel, or a combination thereof The high surface area material can include a textured sidewall surface of the reaction chamber. The high surface area material can include removable particles that can be transferred out of the reaction chamber following a synthesis process.

According to various embodiments, a method of synthesizing a polynucleotide sequence is provided. The method can be carried out, at least in part, in a fluid processing device that includes a reaction chamber and first and second input openings in fluid communication with the reaction chamber. The method can include introducing a first nucleotide monomer into the second input opening of the fluid processing device, moving the first nucleotide monomer by capillary action from the second input opening into the reaction chamber, and attaching the first nucleotide monomer to a support disposed in the reaction chamber to form a first supported nucleotide monomer.

According to various embodiments, the method can include introducing a first deprotecting reagent into the first input opening, and moving the first deprotecting reagent by capillary action from the first input opening into the reaction chamber to form a deprotected first nucleotide monomer in the reaction chamber. The method can include introducing a wash reagent into the first input opening, moving the wash reagent by capillary action from the first input opening into the reaction chamber, and moving the first deprotecting reagent out of the reaction chamber.

The method can include introducing a second nucleotide monomer into the second input opening, and moving the second nucleotide monomer by capillary action from the second input opening into the reaction chamber. A wash reagent can be introduced into the first input opening, can be moved by capillary action from the first input opening into the reaction chamber, and can be moved out of the reaction chamber. The method can include contacting the second nucleotide monomer with the deprotected first nucleotide monomer in the reaction chamber to form a second supported nucleotide monomer.

According to various embodiments, an oligonucleotide or polynucleotide synthesis method is provided that can include moving additional nucleotide monomer, deprotecting reagent, and wash reagent, into the reaction chamber, for example, in the manner described above, to form the desired polynucleotide sequence. The method can further include the steps of moving a cleaving reagent by capillary action into the reaction chamber, and cleaving the second supported polynucleotide sequence from the support to form a cleaved polynucleotide. The cleaved polynucleotide can be retained in or removed from the reaction chamber. Exemplary nucleotide monomers that can be utilized in the method can include a dimethyltrityl-protected phosphoramidite nucleotide monomers, for example.

According to various embodiments, a method of synthesizing an oligonucleotide or a polynucleotide is provided. The method can be carried out in a fluid processing device comprising a reaction chamber and first and second input openings in fluid communication with the reaction chamber. According to various embodiments, the method includes introducing a first nucleotide monomer into the second input opening of the fluid processing device, and moving the first nucleotide monomer by centripetal force from the second input opening into the reaction chamber. The method can include attaching the first nucleotide monomer to a support disposed in the reaction chamber to form a first supported nucleotide monomer. The method can include introducing a first deprotecting reagent into the first input opening, and moving the first deprotecting reagent by centripetal force from the first input opening into the reaction chamber to form a deprotected first nucleotide monomer in the reaction chamber. The method can include moving the first deprotecting reagent out of the reaction chamber, introducing a first wash reagent into the first input opening, and moving the first wash reagent by centripetal force from the first input opening into the reaction chamber.

The method can include introducing a second nucleotide monomer into the second input opening, and moving the second nucleotide monomer by centripetal force from the second input opening into the reaction chamber. The method can include introducing a second wash reagent into the first input opening, moving the second wash reagent by centripetal force from the first input opening into the reaction chamber, and moving the wash reagent out of the reaction chamber. The method can include contacting the second nucleotide monomer with the deprotected first nucleotide monomer in the reaction chamber to form a second supported nucleotide monomer.

The centripetal forces mentioned above can be generated by holding the device to a rotatable platen and rotating the platen.

According to various embodiments, the step of moving the first deprotecting reagent out of the reaction chamber can occur, for example, after or before the step of introducing the first wash reagent into the first input opening. The first, second, and other wash reagents used in the method can be the same as each other or different from one another.

According to various embodiments, the synthesis method can include moving additional nucleotide monomer, deprotecting reagent, and wash reagent, into the reaction chamber, in the order described above, to form a polynucleotide or oligonucleotide sequence. The synthesis method can further include moving a cleaving reagent by centripetal force into the reaction chamber, and cleaving a supported sequence to form a cleaved polynucleotide or oligonucleotide. The cleaved polynucleotide or oligonucleotide can be retained in or removed from the reaction chamber.

According to various embodiments, a polynucleotide sequence synthesis method is provided that can be carried out in a fluid processing device having a substrate, a fluid processing pathway at least partially formed in or on the substrate, and one or more output openings arranged at the output end of the fluid processing pathway and in fluid communication with one or more of a plurality of reaction sites included in the fluid processing pathway. The fluid processing pathway of the processing device can include an input end, at least one output end, a first input opening, a plurality of reaction sites each in fluid communication with the first input opening and positioned between the first input opening and the output end. According to various embodiments, the plurality of reaction sites can each include a high surface area support material therein. The fluid processing pathway can include a plurality of second input openings having two or more input openings in fluid communication respectively with each of the reaction sites. The second input openings can be arranged with the reaction site disposed between the output end and the second input openings.

The synthesis method in a device with a plurality of second input openings for each reaction site can include introducing a first nucleotide monomer into at least one of the reaction sites, and attaching a first protected nucleotide monomer to the high surface area support material in the reaction site. According to various embodiments, the synthesis method can further include deprotecting the first protected nucleotide monomer to form a first deprotected monomer, introducing a wash solution into the reaction site, removing the wash solution from the reaction site, and attaching a second protected nucleotide monomer to the first deprotected monomer to form a protected nucleotide polymer.

According to various embodiments, the synthesis method in a device with a plurality of second input openings for each reaction site can include the additional steps of introducing a wash solution to the reaction site, removing the wash solution from the reaction site, introducing a cleaving reagent into the reaction site, cleaving the protected nucleotide polymer or a derivative from the high surface area support material to form a cleaved polynucleotide, and then removing the cleaved polynucleotide from the reaction site. According to various embodiments, the nucleotide monomers can include, for example, dimethyltrityl-protected phosphoramidite nucleotide monomers.

According to the present teachings, deprotecting a protected nucleotide or protected polynucleotide can include contacting the protected component with an acid, for example, to remove a dimethyltrityl group from a phosphoramidite nucleotide monomer. The acid can be of sufficient strength to accomplish the desired result of removing the protecting group or dimethyltrityl group without undesirable reactions.

All references, patents, patent applications, and patent application publications cited herein are incorporated in their entireties by reference for all purposes.

Those skilled in the art can appreciate from the foregoing description that the present teachings can be implemented in a variety of forms. Therefore, while these teachings have been described in connection with particular embodiments thereof, the teachings should not be so limited. Various changes and modifications can be made without departing from the teachings herein.

What is claimed:

1. A method of synthesizing a polynucleotide sequence comprising:

providing a fluid processing device comprising a reaction chamber and first and second input openings in fluid communication with the reaction chamber;

introducing a protected first nucleotide monomer into the second input opening of a fluid processing device;

moving the protected first nucleotide monomer by capillary action from the second input opening into the reaction chamber;

attaching the protected first nucleotide monomer to a support disposed in the reaction chamber to form a protected first supported nucleotide monomer;

introducing a first deprotecting reagent into the first input opening;

moving the first deprotecting reagent by capillaiy action from the first input opening into the reaction chamber to form a deprotected first supported nucleotide monomer in the reaction chamber;

introducing a wash reagent into the first input opening;

moving the wash reagent by capillary action from the first input opening into the reaction chamber;

moving the first deprotecting reagent out of the reaction chamber;

introducing a protected second nucleotide monomer into the second input opening;

moving the protected second nucleotide monomer by capillary action from the second input opening into the reaction chamber; and contacting the protected second nucleotide monomer with the deprotected first nucleotide monomer in the reaction chamber to form a supported polynucleotide sequence.

2. The method of claim 1, wherein each of the protected first and protected second nucleotide monomers comprises a dimethyltrityl-protected phosphoramidite nucleotide monomer.

3. The method of claim 1, further comprising:

introducing a wash reagent into the first input opening;

moving the wash reagent by capillary action from the first input opening into the reaction chamber; and moving the wash reagent out of the reaction chamber.

4. The method of claim 3, further comprising:

moving additional protected nucleotide monomer, deprotecting reagent, and wash reagent, into the reaction chamber to lengthen the supported polynucleotide sequence.

5. The method of claim 3, further comprising:

moving a cleaving reagent by capillary action into the reaction chamber; and cleaving the supported polynucleotide sequence from the support to form a cleaved polynucleotide sequence.

6. The method of claim 5, further comprising removing the cleaved polynucleotide sequence from the reaction chamber.

7. The method of claim 1, wherein the reaction chamber comprises a high surface area support material.

8. The method of claim 7, wherein the high surface area support material comprises a removable particle, the supported polynucleotide sequence is attached to the removable particle, and the method further comprises removing the supported polynucleotide sequence, attached to the removable particle, from the reaction chamber.

9. The method of claim 7, wherein the high surface area support material comprises a removable particle, the supported polynucleotide sequence is attached to the removable particle, and the method further comprises cleaving the supported polynucleotide sequence from the removable particle.

10. The method of claim 9, wherein the cleaving occurs in the reaction chamber to form a cleaved polynucleotide sequence, and the method further comprises removing the cleaved polyruicleotide sequence from the reaction chamber.

11. The method of claim 9, further comprising removing the supported polynucleotide sequence, attached to the removable particle, from the reaction chamber, wherein the cleaving occurs outside of the reaction chamber.

12. A method of synthesizing a polynucleotide sequence comprising:

providing a fluid processing device comprising a reaction chamber and first and second input openings in fluid communication with the reaction chamber;

introducing a protected first nucleotide monomer into the second input opening of a fluid processing device;

moving the protected first nucleotide monomer by centripetal force from the second input opening into the reaction chamber;

attaching the protected first nucleotide monomer to a support disposed in the reaction chamber to foim a protected first supported nucleotide monomer;

introducing a first deprotecting reagent into the first input opening;

moving the first deprotecting reagent by centripetal force from the first input opening Into the reaction chamber to form a deprotected first supported nucleotide monomer in the reaction chamber;

moving the first deprotecting reagent out of the reaction chamber;

introducing a first wash reagent into the first input opening;

moving the first wash reagent by centripetal force from the first input opening into the reaction chamber;

introducing a protected second nucleotide monomer into the second input opening;

moving the protected second nucleotide monomer by centripetal force from the second input opening into the reaction chamber;and contacting the protected second nucleotide monomer with the deprotected first supported nucleotide monomer in the reaction chamber to form a supported polynucleotide sequence.

13. The method of claim 12, wherein the step of moving the first deprotecting reagent out of the reaction chamber occurs after the step of introducing the first wash reagent into the first input opening.

14. The method of claim 12, wherein the step of moving the first deprotecting reagent out of the reaction chamber occurs before the step of introducing the first wash reagent into the first input opening.

15. The method of claim 12, wherein each of the protected first and protected second nucleotide monomers comprises a dimethyltrityl-protected phosphoramidite nucleotide monomer.

16. The method of claim 12 wherein the fluid processing device further comprises a valve disposed between the second input opening and the reaction chamber and which is capable of interrupting the fluid communication therebetween, and the method further comprises controlling the moving of the protected first nucleotide monomer from the second input opening into the reaction chamber by actuating the valve.

17. The method of claim 12, further comprising:

moving a cleaving reagent by centripetal force into the reaction chamber; and cleaving the supported polynucleotide sequence from the support to form a cleaved polynucleotide sequence.

18. The method of claim 17, further comprising removing the cleaved polynucleotide sequence from the reaction chamber.

19. The method of claim 17, wherein the fluid processing device further comprises an output chamber in fluid communication with the reaction chamber, and the method further comprises moving the cleaved polynucleotide sequence to the output chamber.

20. The method of claim 12, wherein the reaction chamber comprises a high surface area support material.

21. The method of claim 20, wherein the high surface area support material comprises a removable particle, the supported polynucleotide sequence is attached to the removable particle, and the method further comprises removing the supported polynucleotide sequence, attached to the removable particle, from the reaction chamber.

22. The method of claim 20, wherein the high surface area support material comprises a removable particle, the supported polynucleotide sequence is attached to the removable particle, and the method further comprises cleaving the supported polynucleotide sequence from the removable particle.

23. The method of claim 22, wherein the cleaving occurs in the reaction chamber to form a cleaved polynucleotide sequence, and the method further comprises removing the cleaved polynucleotide sequence from the reaction chamber.

24. The method of claim 22, further comprising removing the supported polynucleotide sequence, attached to the removable particle, from the reaction chamber, wherein the cleaving occurs outside of the reaction chamber.

25. The method of claim 12, further comprising:

introducing a second wash reagent into the first input opening;

moving the second wash reagent by centripetal force from the first input opening into the reaction chamber; and moving the second wash reagent out of the reaction chamber.

26. The method of claim 25, wherein the first and second wash reagents are the same.

27. The method of claim 25 wherein the fluid processing device further comprises a valve disposed between the first input opening and the reaction chamber, and capable of interrupting the fluid communication between the reaction chamber and the first input opening, and the method further comprises controlling the moving of the first wash reagent from the first input opening into the reaction chamber by actuating the valve.

28. The method of claim 25, further comprising:

separately moving addition protected nucleotide monomer, deproecting reagent, and wash reagent, into the reaction chamber to lengthen the supported polynucleotide sequence.

29. The method of claim 28, wherein the fluid processing device further comprises a waste chamber in fluid communication with the reaction chamber, and wherein moving the first deprotecting reagent out of the reaction chamber comprises moving the first deprotecting reagent from the reaction chamber to the waste chamber.

* * * * *